United States Patent [19]

Yamaguchi et al.

[11] Patent Number: 5,127,835
[45] Date of Patent: Jul. 7, 1992

[54] PROCESS FOR PREPARATION OF DENTAL CROWN RESTORATION AND KIT FOR USE IN CARRYING OUT SAID PROCESS

[75] Inventors: Koichi Yamaguchi; Shingo Masuda; Keiji Mishima; Michinori Akase; Takahiko Asano, all of Gamou, Japan

[73] Assignee: Kyocera Corporation, Kyoto, Japan

[21] Appl. No.: 254,357

[22] Filed: Oct. 6, 1988

[30] Foreign Application Priority Data

Aug. 6, 1988 [JP] Japan .............................. 63-195322

[51] Int. Cl.$^5$ ............................................. A61C 5/10
[52] U.S. Cl. .................................. 433/222.1; 433/218; 433/223
[58] Field of Search ................... 433/218–219, 433/220, 221, 221.1, 212.1, 223, 203.1

Primary Examiner—Vincent Millin
Attorney, Agent, or Firm—Spensley Horn Jubas & Lubitz

[57] ABSTRACT

Disclosed is a process for the preparation of a dental crown restoration, which comprises preparing a plurality of dental crown-restoring glass materials comprising 100 parts by weight of a glass component and 0.01 to 17.0 parts by weight of an incorporated coloring component and giving colored glass ceramics differing in the value or the combination of the value and chroma in the glass-crystallized state, selecting a shade guide having a color equal or closely akin to the color of a tooth adjacent to the tooth to be restored among a plurality of shade guides classified accord- to a plurality of values or combinations of the value and chroma as one index and a plurality of hues as another index, selecting a glass material giving a predetermined value or a predetermined combination of the value and chroma among said glass materials according to the color of the selected shade guide, preparing a dental crown restoration from the selected glass material, and applying a shading giving a predetermined hue or a predetermined combination of the hue, value and chroma according to the color of the selected shade guide to the surface of the dental crown restoration.

20 Claims, 2 Drawing Sheets

| HUE (X) / COLORED GLASS (P) | $X_1$ | $X_2$ | $X_3$ | $X_4$ |
|---|---|---|---|---|
| $P_1$ | $Q_{11}$ | $Q_{12}$ | $Q_{13}$ | $Q_{14}$ |
| $P_2$ | $Q_{21}$ | $Q_{22}$ | $Q_{23}$ | $Q_{24}$ |
| $P_3$ | $Q_{31}$ | $Q_{32}$ | $Q_{33}$ | $Q_{34}$ |
| $P_4$ | $Q_{41}$ | $Q_{42}$ | $Q_{43}$ | $Q_{44}$ |

FIG. 1

| HUE (X) / COMBINATION (Y) OF VALUE AND CHROMA | $X_1$ | $X_2$ | $X_3$ | $X_4$ |
|---|---|---|---|---|
| $Y_1$ | $Z_{11}$ | $Z_{12}$ | $Z_{13}$ | $Z_{14}$ |
| $Y_2$ | $Z_{21}$ | $Z_{22}$ | $Z_{23}$ | $Z_{24}$ |
| $Y_3$ | $Z_{31}$ | $Z_{32}$ | $Z_{33}$ | $Z_{34}$ |
| $Y_4$ | $Z_{41}$ | $Z_{42}$ | $Z_{43}$ | $Z_{44}$ |

FIG. 2

| HUE (X) / COLORED GLASS (P) | $X_1$ | $X_2$ | $X_3$ | $X_4$ |
|---|---|---|---|---|
| $P_1$ | $Q_{11}$ | $Q_{12}$ | $Q_{13}$ | $Q_{14}$ |
| $P_2$ | $Q_{21}$ | $Q_{22}$ | $Q_{23}$ | $Q_{24}$ |
| $P_3$ | $Q_{31}$ | $Q_{32}$ | $Q_{33}$ | $Q_{34}$ |
| $P_4$ | $Q_{41}$ | $Q_{42}$ | $Q_{43}$ | $Q_{44}$ |

PROCESS FOR PREPARATION OF DENTAL CROWN RESTORATION AND KIT FOR USE IN CARRYING OUT SAID PROCESS

BACKGROUND OF THE INVENTION

(1) Field of the Invention

The present invention relates to a process for the preparation of a dental crown restoration and a kit for use in carrying out this process. More particularly, the present invention relates to a process for the preparation of a dental crown restoration which can reproduce in an artificial tooth a deep color having good esthetics and resembling the color of a natural tooth and can be easily processed. Furthermore, the present invention relates to an artificial tooth of a novel composition.

(2) Description of the Prior Art

Ceramics now developed as biomaterials, such as alumina, zirconia, carbon, silicon nitride and calcium phosphate ceramics are excellent over conventional anti-corrosive alloys such as stainless steels and nickel-cobalt alloys. Castable ceramics for dental crown restoration materials, that is, crystalline glass ceramics to be applied to cast-forming, are now regarded as being promising. Since the material of this type is prepared by the lost-wax process, reproduction can be accomplished more easily than in the conventional porcelain build-up process and even a fine part can be reproduced faithfully, and a high experience technique becomes unnecessary.

The specification of U.S. Pat. No. 4,650,418 discloses a dental prosthetic facing comprising an outer shader layer, an intermediate at least substantially uncolored translucent layer, and an opaque substrate color-keyed with said shader to match a shade guide. It is taught that this uncolored translucent layer is formed of mica ceramic glass.

Furthermore, the specification of U.S. Pat. No. 4,189,325 discloses a glass-ceramic dental restoration comprising $LiO_2$, $CaO$, $Al_2O_3$ and it is taught that the restoration can be colored by incorporation of one or more inorganic coloring agents.

Moreover, European Patent Application 0022655 discloses a prosthetic material formed by casting and crystallizing a glass ceramic of the mica composition, and it is taught that various colorants can be incorporated into this ceramic.

Still further, Japanese Patent Application Laid-Open Specification No. 69007/85 discloses an artificial dental crown composed of a glass ceramic in which crystallites of a calcium phosphate type mineral composed mainly of apatite are formed, and it is taught that the back surface of the dental crown is colored with a coloring agent. Japanese Patent Application Laid-Open Specification No. 96544/85 teaches that a crystallized glass of the calcium phosphate type composed mainly of apatite and having a Ca/P atomic ratio of 0.35 to 1.7 is colored by incorporating one or more transition metal oxides and rare earth element oxides.

Generally, 16 to 24 kinds of shade guides are used for making the shade of an artificial tooth inclusive of a dental crown in agreement with or closely akin to the shade of an adjacent tooth.

According to the above-mentioned teaching of U.S. Pat. No. 4,650,418, the outer shader layer is combined with the opaque substrate through the translucent intermediate layer to produce a color matched with a shade guide. However, even according to this teaching, it is still difficult to reproduce a deep color resembling the color of a natural tooth. More specifically, the interior of a natural tooth is composed of colored dentine and the surface is composed of substantially uncolored transparent enamel. In contrast, the above-mentioned artificial tooth has a reverse structure and a color lacking depth is likely formed. Moreover, in order to produce a predetermined color in the outer shader layer, the operation of coating a shading composition and firing the coating should be repeated many times, for example, at least 6 times, and the processing operation becomes complicated. Moreover, if the shader layer is worn, the uncolored translucent layer is exposed and the color of the artificial tooth is drastically changed, and the allowance of the durability or life of the artificial tooth is relatively narrow.

According to the conventional technique of coloring a glass ceramic per se, an artificial tooth having a good durability and a color akin to the color of a natural tooth can be stably prepared, but a variety of pigment-incorporated glass ceramic compositions should be prepared according to the shade guides.

In the conventional crystallized glass ceramic of the calcium phosphate type composed mainly of apatite and having a Ca/P atomic ratio of 0.35 to 1.7, opacification or whitening by the crystallization is conspicuous, and the appearance of the ceramic is quite different from the appearance of a natural tooth. Moreover, even if this apatite type ceramic is colored by internal addition of a pigment or by coating with a shading composition, it is difficult to reproduce a somewhat translucent appearance of a natural tooth.

SUMMARY OF THE INVENTION

It is therefore a primary object of the present invention provide a process for the preparation of a dental crown restoration which can reproduce in an artificial tooth a deep color having good esthetics and resembling the color of a natural color and can be easily processed.

Another object of the present invention is to provide a convenient kit for the restoration of a dental crown, by which a dental crown restoration having the above-mentioned characteristics can be easily prepared.

Still another object of the present invention is to provide an artificial tooth having a translucency controlled to a level close to the translucency of a natural tooth and having a deep color and appearance resembling those of the natural tooth, though the artificial tooth is composed mainly of an apatite glass ceramic.

In accordance with one aspect of the present invention, there is provided a process for the preparation of a dental crown restoration, which comprises preparing a plurality of dental crown-restoring glass materials comprising 100 parts by weight of a glass component and 0.01 to 17.0 parts by weight of an incorporated coloring component and giving colored glass ceramics differing in the value or the combination of the value and chroma in the glass-crystallized state, selecting a shade guide having a color equal or closely akin to the color of a tooth adjacent to the tooth to be restored among a plurality of shade guides classified accord- to a plurality of values or combinations of the value and chroma as one index and a plurality of hues as another index, selecting a glass material giving a predetermined value or a predetermined combination of the value and chroma among said glass materials according to the color of the selected shade guide, preparing a dental crown restoration from the selected glass material, and applying a shading giving a predetermined hue or a predetermined combination of the hue, value and chroma according to the color of the selected shade guide to the surface of the dental crown restoration.

In accordance with another aspect of the present invention, there is provided a kit for the restoration of dental crowns, which comprises shade guides classified by a plurality of values or a plurality of combinations of the value and chroma as one index and a plurality of hues as another index, a package comprising plurality of crown-restoring glass materials comprising 100 parts by weight of a glass component and 0.01 to 17 parts by weight of an incorporated coloring component and giving colored glass ceramics differing in the value or the combination of the value and chroma in the crystallized state, said glass materials being filled in vessels corresponding to the respective value indexes, and a package comprising a plurality of shading compositions comprising 60 to 95% by weight of a sodium silicate having a melting point of 500° to 1000° C. and 5 to 40% by weight of a coloring agent and differing in the hue or the combination of the hue, value and chroma, said shading compositions being filled in vessels corresponding to the respective hue or value-hue indexes.

In accordance with still another aspect of the present invention, there is provided an artificial tooth consisting of a colored crystallized glass composed mainly of apatite, said colored glass comprising 100 parts by weight of a glass component and 0.01 to 17 parts by weight of a coloring component, said glass component comprising 40 to 80% by weight of a $CaO-P_2O_5$ component having a Ca/P atomic ratio of 2.5 to 4.0 and 20 to 60% by weight of an $SiO_2MgO$ component, and said coloring component being an oxide of an least one metal selected from the group consisting of Ce, Pr, Eu, Ti, V, Cr, Mn, Fe, Co, Ni, Zr, Nb, Mo, Ag and W.

BRIEF DESCRIPTION OF THE DRAWINGS

FIG. 1 is a table of classification of shade guides (Z) by the combination (Y) of the value and chroma relative to the hue (X).

FIG. 2 is a table of reproduction classification of shade guides by the combination of the colored glass material (P) and the shading composition (Q).

DETAILED DESCRIPTION OF THE PREFERRED EMBODIMENTS

There are many color systems for indicating a color of a body. According to the Munsell color system, the color is indicated by three elements, that is, hue, value and chroma. The hue is defined by five hues of red (R), yellow (Y), green (G), blue (B) and purple (P) and five intermediates hues such as yellowish red (YR). The value indicates the light and darkness, and 0 means the darkest and 10 means the lightest. The chroma indicates the sharpness of the color, and 0 means no chroma and the value of the chroma increases as the sharpness increases.

By Yamazaki et al., it is reported that according to the Munsell color system, the color of a natural tooth has a hue of 8.75 YR-1.25Y, a value of 8.0-5.5 and a chroma of N6.5-1.25 Y, 6.5/4.5.

In the present invention, shade guides classified by (i) a plurality of values or a plurality of combinations of the value and chroma as one index and (ii) a plurality of hues as another index are prepared. The shade guides are arranged so that a color specified by the above classification is manifested when a shading layer is applied to a colored glass ceramic as described in detail hereinafter.

Referring to FIG. 1 showing an example of the table of classification of shade guides, the ordinate Y represents the grade (index) of the value or the combination of the value and chroma, and for example, the value is reduced in order of $Y_1, Y_2 \ldots$ On the other hand, the abscissa X indicates the grade (index) of the hue, and for example, the above-mentioned range of 8.75Y-1.25Y is classified in a plurality of grades $X_1, X_2, X_3, \ldots$. Shade guides $Z_{11}, Z_{21}, \ldots$ are fitted in columns and lines defined by respective grades of the abscissa and ordinate X-Y. The kinds of the shade guides may be 16 or 24 as customarily used, but they are not limited to those customarily used and the number of the kinds may be larger or smaller. If there is no substantial distinction of colors between adjacent columns and lines, the shade guide in one column and line may be omitted.

According to the present invention, a plurality of dental crown-restoring glass materials giving colored glass ceramics differing in the value or the combination of the value and chroma in the crystallized state and a plurality of shading compositions differing in the hue and the combination of the hue, value and chroma are prepared, and the dental crown-restoring material and shading composition are selected according to the selected shade guide. The dental crown-restoring glass material is a composition comprising 100 parts by weight of a glass component and 0.01 to 17.0 parts by weight, preferably 0.03 to 6.0 parts by weight, of a coloring component. The melt of this composition is cast in a mold prepared, for example, according to the lost-wax method and having a cavity corresponding to the dental crown, and the cast product is heat-treated to crystallize the glass, whereby a dental crown restoration proper composed of a colored glass ceramic is obtained. The shading composition comprises 60 to 95% by weight, preferably 70 to 90% by weight, of a sodium silicate glass having a melting point of 500° to 1000° C., especially 600° to 900° C., and 5 to 40% by weight, preferably 10 to 30% by weight, of a coloring agent. This composition is coated on the dental crown restoration proper, and the coating is fired and the coating-firing operation is repeated according to need, whereby a dental crown restoration having a desired color is obtained.

More specifically, FIG. 1 shows the table of classification of shade guides (Z) according to the combination (Y) of the value and chroma relatively to the hue (X), and in this classification table, the hue (X) is selected within the range of 8.75YR-1.25Y expressed by the Munsell color system and the hue is changed from yellowish red to yellow, that is, from $X_1$ to $X_4$. The combination (Y) of the value and chroma is selected from the value range of 9.0-5.0 and the chroma range of 8.0-0, expressed by the Munsell color system. $Y_1$ corresponds to 9.0/4.5 and $Y_4$ corresponds to 6.5/4.5, and the value is reduced toward $Y_4$ from $Y_1$.

For example, $Z_{23}$ is selected as the shade guide having a color equal or akin to the color of the tooth adjacent to the tooth to be restored among the shade guides in the classification table of FIG. 1. The value index $Y_2$ and the chroma index $X_3$ are determined according to this shade guide $Z_{23}$. Then, a classification table for reproduction of shade guides according to the combination of the colored glass material (P) and the shading composition (Q), which is shown in FIG. 2, is referred to. In this reproduction classification table, a dental crown restoration substrate is prepared by using the preliminarily prepared colored glass material $P_2$ corresponding to the value index $Y_2$ shown in FIG. 1, and a shading layer is formed on the substrate by using the preliminarily prepared shading composition $Q_{23}$ corresponding to the hue index $X_3$ or the shade guide $Z_{23}$, whereby a dental crown restoration having the same color as that of the shade guide $Z_{23}$ is obtained.

Incidentally, the colored glass materials $P_1$ through $P_4$ corresponding to the value indexes $Y_1$ through $Y_4$, respectively, have substantially the same hues in the crystallized state, and the hues are selected within the range of 7.5YR-2.5Y expressed by the Munsell color system. For example, if these hues are set at 8.75YR as the hue index $X_1$, the hue of the shade guides $Z_{11}$, $Z_{21}$, $Z_{31}$ and $Z_{41}$ can be reproduced without forming the shading layer. In this case, shading for adjusting the value and chroma will be conducted, if necessary.

The color of the dental crown restoration as a whole in the present invention is manifested by the combination of the dental crown restoration proper composed of the colored glass ceramic and the shading layer formed thereon. Since not only the surface of the dental crown restoration but also the interior thereof is colored according to the value or chroma of the tooth, the dental crown restoration of the present invention is advantageous in that a deep color closely akin to the color of a natural tooth and an appearance closely akin to that of a natural tooth can be reproduced. Furthermore, since not only the shading layer but also the dental crown restoration proper located below is colored, even if the shading layer is worn away, a drastic change of the color of the surface of the dental crown restoration can be avoided and the allowance of the durability or life is broadened. Moreover, since the dental crown restoration proper is colored, the degree of coloration by the shading layer can be reduced and the frequency of coating or baking of the shading layer can be decreased, and the color unevenness which is due to the uneven thickness of the shading layer is not conspicuous and the processing can be facilitated. Still further, by selection of the shade guide, the combination of the glass material and shading composition can be specified and dental crown restorations having the same color and appearance can always be obtained with a good reproducibility.

The dental crown-restoring glass material used in the present invention is a calcium phosphate type glass, especially a glass having a composition of $CaO-P_2O_5-MgO-SiO_2$, and in view of the mechanical strength, durability and safety of the dental crown restoration, it is preferred that the dental crown restoration proper obtained by casting and heat-treating the glass be a colored crystallized glass composed mainly of apatite.

In accordance with a most preferred embodiment of the present invention, the colored crystallized glass composed of apatite has such a striking characteristic that the transparency (Ts) defined by the following formula is 20 to 70:%, especially 30 to 60%:

$$Ts = (Ys/Yo) \times 100$$

wherein Ys stands for Y value of the tristimulus values of the transmitted light in the standard colorimetric system CIE, measured at a visual field angle 2° by using standard illuminant C with respect to a disk-shaped colored crystallized glass having a thickness of 1.25 mm, and Yo stands for Y value determined with respect to the above-mentioned standard illuminant in the same manner as described above except that the colored crystallized glass is not placed.

As pointed out hereinbefore, in the conventional glass ceramic composed mainly of apatite, opacification is extreme because of prominent growth of grains of apatite by crystallization, and therefore, the transparency (Ts) measured according to the above-mentioned method is generally lower than 30%. Accordingly, an artificial tooth formed by using apatite is white and has a feel or appearance quite different from that of a natural tooth, and gives an impression of a man-made product. This tendency is similarly observed when the ceramic is colored by internal addition of a pigment or when the ceramic is colored by coating with a shading composition. In contrast, although the apatite ceramic used in the present invention is somewhat transparent, since the ceramic is colored, a good combination of translucency and deep color resembling those of a natural tooth can be obtained. In the apatite ceramic of the present invention, if the transparency (Ts) is too low and below the above-mentioned range, the dental crown becomes opaque and the natural feel is substantially lost. If the transparency (Ts) is too high and exceeds the above-mentioned range, the color or appearance of the dental crown is often influenced by the lower structure, such as a cement or metal foundation. In a glass material giving a colored glass having a low value among a plurality of glass materials used in the present invention, it is preferred that the transparency (Ts) be 30 to 70%, especially 35 to 60%, and in a glass material giving a colored glass having a high value, it is preferred that the transparency (Ts) be 20 to 60%, especially 30 to 50%.

In order to obtain a crystallized colored glass having a transparency (Ts) included within the above-mentioned range, it is preferable to use a composition comprising 40 to 80% by weight, especially 50 to 70% by weight, of a $CaO-P_2O_5$ component having a Ca/P atomic ratio of from 2.5 to 4.0, especially from 2.9 to 3.9, and 20 to 60% by weight, especially 25 to 50% by weight, of an $SiO_2-MgO$ component, though compositions that can be used in the present invention are not limited to the above-mentioned composition.

Apatite is expressed, for example, by the formula of $Ca_5(F, Cl)P_3O_{12}$ and the Ca/P atomic ratio is 1.67. In contrast, in the present invention, the Ca atom is excessive over the P atom. The excess of the Ca atom reacts with $SiO_2$ of the second component to form a vitreous phase.

This will now be described with reference to the following reaction formulae.

$$CaO + P_2O_5 \rightarrow apatite \quad (1)$$

$$CaO + SiO_2 \rightarrow wollastonite \quad (2)$$

$$CaO + P_2O_5 + SiO_2 \rightarrow apatite + glass\ (wollastonite) \quad (3)$$

In the system including the reaction (1) alone, apatite is easily formed. If the system (2) is added to the system (1), formation of apatite is controlled by formation of the glass, as indicated by the reaction (3).

In the case where the Ca/P atomic ratio lower than 2.5 in the $CaO-P_2O_5$ component, crystallization is promptly advanced and control of crystallization is difficult, and opacification tends to be excessively prominent. If the Ca/P atomic ratio is higher than 4.0, the amount formed of apatite decreases and the transparency becomes too high. The proportion (% by weight) of the $CaO-P_2O_5$ component is determined for the same reason as described above. If the proportion of the $CaO-P_2O_5$ component is higher than 80% by weight, the amount formed of apatite is too large and opacification becomes extreme. If the proportion of the $CaO-P_2O_5$ component is lower than 40% by weight, the amount formed of apatite is too small and the transparency (Ts) exceeds 70%.

The $SiO_2/MgO$ weight ratio can be changed within a broad range, but it is generally preferred that this weight ratio is from 2 to 100, especially from 2 to 20.

In general, a member selected from the group consisting of rare earth metal oxides and transition metal oxides is generally preferred as the coloring component incorporated in the starting glass. Ce, Pr and Eu can be mentioned as the rear earth metal, and Ti, V, Cr, Mn, Fe, Co, Ni, Zr, Nb, Mo, Ag and W can be mentioned as the transition metal. The kind of the used metal oxide depends on the color of the colored glass ceramic.

Coloring agents for glass are reported in many literature references, but the number of coloring agents giving colors of yellow and red systems necessary for dental crowns, which are stable at high temperatures, are very small, and since the coloring agents are influenced by the kind of the base glass, the number is much limited. Among these coloring agents, we have found coloring components suitable for reproducing a dental crown color in the above-mentioned calcium phosphate type glass having a Ca/P atomic ratio of 2.5 to 4.0. $Ce_2O_3$ gives a yellow tint, and if the amount is smaller than 10% by weight, the effect is not attained and if the amount exceeds 70% by weight, the yellow tint becomes excessive. $Mn_3O_4$ gives a red tint, and if the amount is smaller than 30% by weight, the effect is low and addition of $Mn_3O_4$ in an amount exceeding 70% by weight is insignificant because the coloration is saturated. By addition of up to 15% by weight of $Fe_3O_4$, the coloration by $Mn_3O_4$ is assisted. If $Fe_3O_4$ is added in an amount larger than 15% by weight, the chroma is reduced and the color becomes dark. If $TiO_2$ is added in an amount of up to 40% by weight, a yellow tint is manifested as well as by $Ce_2O_3$, and simultaneously, $TiO_2$ reacts with MgO of the base glass to precipitate a crystal of magnesium titanate and assist the opacification. If the amount added of $TiO_2$ exceeds 40% by weight, in general, the opacification becomes too conspicuous. Since $Al_2O_3$ or $ZrO_2$ increases the transparency, in the case where $TiO_2$ is added together with $Al_2O_3$ or $ZrO_2$, $TiO_2$ may be added in an amount of up to about 70% by weight, but the coloring effect by $TiO_2$ is set off and increase of the amount of $TiO_2$ is insignificant. If $V_2O_5$ is added in an amount of up to 10% by weight, $V_2O_5$ exerts an effect of giving a red tint together with $Ce_2O_3$ and also exerts an effect of lowering the melting point. However, if the amount of $V_2O_5$ exceeds 10% by weight, a green tint is manifested and no good results can be obtained.

In view of the foregoing, it is preferred that a composition comprising 10 to 70% by weight based on the coloring component of $Ce_2O_3$, 30 to 70% by weight based in the coloring component of $Mn_3O_4$, up to 40% by weight base on the coloring component of $TiO_2$, up to 15% by weight based on the coloring component of $Fe_3O_4$ and up to 10% by weight based on the coloring component of $V_2O_5$ be used as the coloring component for the calcium phosphate type glass having a Ca/P atomic ratio of 2.5 to 4.0.

In the present invention, for the production of glass materials differing in the value or the combination of the value nd chroma, it is preferred that the amount incorporated of the above-mentioned coloring composition or the amounts of respective components of the composition be changed. For example, for increasing the value, the amount incorporated of the coloring composition is reduced, and for decreasing the value, the amount incorporated of the coloring composition is increased.

The shading composition used in the present invention is a composition comprising a sodium silicate glass and a coloring agent, as pointed out hereinbefore. Any of sodium silicate glasses having a melting point included within the above-mentioned range can be used, and in general, a sodium silicate glass having the following composition is used.

| Component | General Range (% by weight) | Preferred Range (% by weight) |
| --- | --- | --- |
| $SiO_2$ | 55-80 | 60-75 |
| $Na_2O$ | 2-15 | 3-10 |
| $K_2O$ | 0-10 | 1-5 |
| $B_2O_3$ | 0-15 | 2-10 |
| $Al_2O_3$ | 0-10 | 1-8 |
| ZnO | 2-25 | 5-20 |

Any of inorganic pigments (metal oxide pigments) customarily used for conventional shading compositions can be used as the pigment in the shading composition. For example, there can be mentioned $ZrO_2$, and $SnO_2$, $V_2O_5$, CaO, $SiO_2$, $Cr_2O_3$, $Al_2O_3$, ZnO, $Fe_2O_3$, $Sb_2O_3$, CoO, NiO and $TiO_2$, and these pigments are used in the form of mixtures of two or more of them. Shading compositions differing in the hue can be obtained by changing the amounts and combination of the incorporated pigments, and shading compositions differing in the value and chroma can be obtained by changing the amounts incorporated of the pigments.

In the present invention, the shading layer may be a single layer composed of a single composition or a plurality of layers differing in the composition. It must be understood that this shading layer may comprise, for example, an undercoat layer of a basic color of each shade and a topcoat layer reproducing each shade.

In accordance with another embodiment of the present invention, there is provided a kit for restoring dental crowns, which comprises the above-mentioned shade guides, a package comprising a plurality of dental crown-restoring glass materials filled in vessels corresponding to the value indexes of the shade guides, respectively, and a package comprising a plurality of shading compositions filled in vessels corresponding to the hue indexes or the value-hue indexes, respectively. By utilizing this kit, a dental crown restoration having a desired color can be easily prepared with a good reproducibility in a dentist's office or technician's office. More specification, since shade guides $Z_{11}$, $Z_{22}$, .... shown in the classification tables of FIGS. 1 and 2, glass materials $P_1$, $P_2$, .... packaged in vessels and shading compositions $Q_{11}$, $Q_{21}$, .... packaged in vessels are provided in the form of a kit, in a dentist's office or technician's office, based on the indexes of the shade guides of this kid, a dental crown restoration proper of a colored glass ceramic can be prepared from the glass material and a shading layer coating can be prepared from the shading composition.

If the glass material for restoring a dental crown is filled in the form of tablets in a vessel also acting as a crucible, casting for formation of a dental crown restoration can be simply and easily performed without contamination with other glass component or the like. In order to facilitate the coating operation, it is preferred that the shading composition be filled in a vessel in the form of a fine powder.

Casting for formation of a dental restoration is carried out at a temperature higher than the melting temperature of the glass material, preferably 1000° to 1600° C., especially preferably 1200° to 1530° C. It is preferred that the heat treatment for the crystallization to apatite be carried out at a temperature of 600° to 1100° C., especially 700° to 950° C., for 10 to 1000 minutes. In order to remove the strain from the cast product, annealing of the cast product can be carried out at a temperature slightly lower than the crystallization temperature. The obtained cast product can be subjected to post treatments such as polishing and washing.

For formation of the shading layer, the powder of the shading composition is dispersed in a coating medium to form a coating composition. As the coating medium, there are advantageously used, for example, water, ethylene glycol, glycerol, ethyl alcohol, methyl alcohol, triethanolamine and diacetone alcohol. The coating composition is uniformly coated on the surface of the cast product by using a coating tool such as a brush. The coated cast product is heated at, for example, 50° to 500° C. to evaporate or volatilize the coating medium, and then, the coated cast product is heated at 500° to 1000° C. to melt the shading composition on the surface of the cast product and fire the shading composition to the surface of the cast product. These operation can be repeated a plurality of times according to need. Thus, a shading layer is formed.

The present invention will now be described in detail with reference to the following examples that by no means limit the scope of the invention.

EXAMPLE 1

Preparation of Colored Glass for Restoration of Dental Crown

A base glass was prepared by mixing 61.1% by weight of $CaO-P_2O_5$ having a Ca/P atomic ratio of 3.54, 34.4% by weight of $SiO_2$ and 4.4% by weight of MgO.

$Ce_2O_3$, $Mn_3O_4$, $TiO_2$, $Fe_3O_4$ and $V_2O_5$ were added as the coloring components for coloring the base glass in a yellowish brown color of the natural dental crown, as shown in Table 1.

TABLE 1

| Colored Glass | Coloring Component Composition | | | | | Base Glass |
|---|---|---|---|---|---|---|
| | $Ce_2O_3$ | $Mn_3O_4$ | $TiO_2$ | $Fe_3O_4$ | $V_2O_5$ | |
| $P_1$ | 0.16 | 0.18 | 0.02 | 0.04 | 0.01 | 99.59 |
| | (39) | (44) | (5) | (10) | (2) | |
| $P_2$ | 0.17 | 0.23 | 0.03 | 0.06 | 0.01 | 99.50 |
| | (34) | (46) | (6) | (12) | (1) | |
| $P_3$ | 0.21 | 0.36 | 0.04 | 0.09 | 0.01 | 99.29 |
| | (30) | (51) | (6) | (13) | (1) | |
| $P_4$ | 0.22 | 0.39 | 0.05 | 0.10 | 0.01 | 99.23 |

TABLE 1-continued

| Colored Glass | Coloring Component Composition | | | | | Base Glass |
|---|---|---|---|---|---|---|
| | $Ce_2O_3$ | $Mn_3O_4$ | $TiO_2$ | $Fe_3O_4$ | $V_2O_5$ | |
| | (29) | (51) | (7) | (13) | (1) | |

Note

The unit of each value is % by weight, and each parenthesized value indicates the content (% by weight) based on the coloring component composition.

The formed composition was molten at 1500° C. over a period of 1 hour and then cooled to form a glass frit. The glass frit was re-molten at 1510° C. over a period of 2 minutes. A casting mold for forming test piece of 16 mm × 16 mm × 1.5 mm, which was preheated at 600° C. was set in a centrifugal casting machine (Model CP-CAST701 supplied by Denken Co., Ltd.), and the re-molten glass was centrifugally cast. Then, the cast product was annealed at 600° C. for 1 hour and at 700° C. for 10 minutes in a burning-out furnace (Model CP-RING301 supplied by Denken Co., Ltd.), and the casting mold was cooled to room temperature and the cast product was taken out from the mold. The cast product was set in a crystallization furnace (Model CP-CRYSTAL501 supplied by Denken Co., Ltd.) and heat-treated at 900° c. for 1 hour to effect crystallization. Thus, plate-shaped test pieces corresponding to colored glasses $P_1$, $P_2$, $P_3$ and $P_4$ were obtained.

Both the surfaces of the plate-shaped test piece were polished flatwise so that the thickness was reduced to 1.25 mm. of the tristimulus values of the standard colorimetric system CIE, the Y value (Ys) of the transmitted light was measured at a visual field angle of 2° through the test piece by using the standard illuminant C, and similarly, the Y value (Yo) was measured without setting the test piece. The transparency (Ts) was calculated according to the formula of $Ts=(Ys/Yo)\times 100$. It was found that the transparencies (Ts) of the colored glasses $P_1$, $P_2$, $P_3$ and $P_4$ were 38%, 40%, 44% and 48%, respectively. From these results, it is seen that the transparency (Ts) increases in order of the colored glasses $P_1$, $P_2$, $P_3$ and $P_4$, that is, as the value of the dental crown to be reproduced by the colored glass is lower. Incidentally, the hue of each of the colored glasses $P_1$, $P_2$, $P_3$ and $P_4$ is about 10YR.

EXAMPLE 2

Change of Composition of Base Glass

In order to examine changes of the physical properties of the colored glass caused when the composition of the base glass was changed test pieces of samples 1 through 9 were prepared in the same manner as described in Example 1 by using the coloring component composition for the colored glass $P_2$, shown in Example 1, and a base glass having a composition shown in Table 2. The transparency (Ts), the castability and the flexural strength were determined. The obtained results are shown in Table 2. Incidentally, the castability was evaluated according to the following standard:

○: sample having a glass melting temperature lower than 1400° C.

△: sample having a glass melting temperature of 1400° to 1500° C.

X: sample having a glass melting temperature higher than 1500° C.

TABLE 2

| Sample No | CeO (% by weight) | $P_2O_5$ (% by weight) | $SiO_2$ (% by weight) | MgO (% by weight) | Coloring Component (% by weight) | Ca/P Atomic Ratio | Ts Value | Castability | Flexural Strength (Kg/mm²) |
|---|---|---|---|---|---|---|---|---|---|
| 1 | 45.0 | 16.2 | 33.8 | 4.5 | 0.5 | 3.52 | 51% | O | 32 |
| 2 | 44.5 | 16.5 | 34.2 | 4.3 | 0.5 | 3.41 | 46% | O | 30 |
| 3 | 43.7 | 16.5 | 35.3 | 4.0 | 0.5 | 3.35 | 30% | O | 29 |
| 4 | 43.5 | 17.3 | 35.2 | 3.5 | 0.5 | 3.18 | 26% | O | 27 |
| 5 | 39.8 | 18.0 | 38.2 | 3.5 | 0.5 | 2.8 | 22% | O | 23 |
| 6 | 37.9 | 20.0 | 38.1 | 3.5 | 0.5 | 2.4 | 16% | O | 19 |
| 7 | 48.9 | 15.1 | 32.0 | 3.5 | 0.5 | 4.1 | 73% | O | 18 |
| 8 | 26.1 | 10.0 | 58.9 | 4.5 | 0.5 | 3.3 | 19% | X | — |
| 9 | 60.0 | 23.0 | 12.0 | 4.5 | 0.5 | 3.3 | 61% | Δ | — |

As is apparent from the results shown in Table 2, with decrease of the Ca/P atomic ratio, the transparency (Ts) decreases and the translucency increases. In sample 6, the Ca/P atomic ratio was 2.4, and the translucency was extreme. In sample 7, the Ca/P atomic ratio was 4.1, and the transparency was too high. In samples 8 and 9, the glass melting temperature was higher than 1400° C. and the castability was poor. Accordingly, these samples are not colored glass compositions suitable for the present invention.

EXAMPLE 3

Change of Composition of Coloring Component

In order to confirm coloring effects by various coloring component compositions, coloring components shown in Table 3 were added to the base glass material used in Example 1, and in the same manner as described in Example 1, test pieces of samples 10 through 26 were prepared and the hue and value were determined. The obtained results are shown in Table 3.

the samples 16 through 18 can be used as the colored glass material $P_3$ corresponding to the value index $Y_3$, and the samples 19 through 21 can be used as the colored glass material $P_4$ corresponding to the value index $P_4$. In view of the identity of the hue, for example, the samples 10, 13, 16 and 19 can be used as the colored glass materials $P_1$, $P_2$, $P_3$ and $P_4$, respectively. The samples 23 through 26 were not suitable for the present invention in the value or the color.

EXAMPLE 4

Preparation of Shading Composition

A base glass, shown in Table 4, for a shading composition was prepared, and the base glass was molten at 1300° C. for 10 hours to prepare a frit. The base glass frit was pulverized and coloring components, shown in Table 4, for a shading composition were added to the pulverized frit, and the mixture was calcined at 700° C. for 1 hour and pulverized to a size of about 3 μm. Thus, shading compositions $Q_{11}$, $Q_{21}$, . . . $Q_{34}$ and $Q_{44}$ were

TABLE 3

| Sample No. | Coloring Component Composition (% by weight) | | | | | | | Amount (% by weight) of coloring Components in Colored Glass Material | Value | Hue after Crystallization |
|---|---|---|---|---|---|---|---|---|---|---|
| | $Ce_2O_3$ | $Mn_3O_4$ | $Fe_3O_4$ | $TiO_2$ | $V_2O_5$ | $Al_2O_3$ | $ZrO_2$ | | | |
| 10 | 41 | 42 | 7 | 10 | 0 | 0 | 0 | 0.3 | 9 | reddish yellowish brown |
| 11 | 30 | 32 | 5 | 22 | 2 | 7 | 2 | 4.7 | 9 | brown |
| 12 | 21 | 32 | 3 | 35 | 1 | 7 | 1 | 11.8 | 9 | " |
| 13 | 31 | 51 | 6 | 12 | 0 | 0 | 0 | 0.5 | 8 | reddish yellowish brown |
| 14 | 23 | 38 | 5 | 26 | 6 | 6 | 1 | 5.1 | 8 | brown |
| 15 | 19 | 33 | 3 | 34 | 3 | 7 | 1 | 12.7 | 8 | " |
| 16 | 24 | 55 | 7 | 14 | 0 | 0 | 0 | 0.7 | 7 | reddish yellowish brown |
| 17 | 19 | 43 | 6 | 23 | 6 | 7 | 1 | 6.4 | 7 | brown |
| 18 | 13 | 32 | 4 | 38 | 3 | 7 | 2 | 13.5 | 7 | " |
| 19 | 23 | 56 | 7 | 14 | 0 | 0 | 0 | 0.8 | 6 | reddish yellowish brown |
| 20 | 20 | 46 | 6 | 21 | 1 | 5 | 1 | 7.5 | 6 | brown |
| 21 | 15 | 35 | 5 | 36 | 2 | 6 | 1 | 14.0 | 6 | " |
| 22 | 10 | 30 | 1 | 47 | 1 | 11 | 0 | 5.2 | 7 | " |
| *23 | 25 | 32 | 5 | 28 | 2 | 6 | 2 | 25.1 | 4 | grayish brown |
| *24 | 80 | 10 | 5 | 2 | 2 | 1 | 0 | 1.2 | 7 | yellow |
| *25 | 5 | 80 | 10 | 3 | 1 | 1 | 0 | 1.0 | 6 | reddish purple |
| *26 | 15 | 32 | 40 | 10 | 1 | 1 | 1 | 1.0 | 4 | yellowish green |

Note
*: not suitable for the present invention

It was found that of the samples 10 through 26, the samples 10 through 12 can be used as the colored glass material $P_1$ corresponding to the value index $Y_1$ in FIG. 1, the samples 13 through 15 can be used as the colored glass material $P_2$ corresponding to the value index $Y_2$, prepared.

The powder of each shading composition was press-molded and calcined at 700° C. for 1 hour, and the hue of the obtained disk-shape test piece was observed. The obtained results are shown in Table 5.

TABLE 4

(unit: % by weight)

| Shading Composition | ZrO$_2$ | SnO$_2$ | V$_2$O$_5$ | CaO | SiO$_2$ | Cr$_2$O$_3$ | Al$_2$O$_3$ | ZnO | Fe$_2$O$_3$ | Sb$_2$O$_3$ | CoO | NiO | Base Glass |
| --- | --- | --- | --- | --- | --- | --- | --- | --- | --- | --- | --- | --- | --- |
| Q$_{11}$ | 8.5 | 2.2 | 0.1 | 0.3 | 0.4 | 0.2 | 0.2 | 0.5 | 0.2 |  |  |  | 87.4 |
| Q$_{21}$ | 7.0 | 1.8 |  | 0.6 | 0.8 | 0.5 | 0.6 | 1.5 | 0.6 | 0.1 |  |  | 86.6 |
| Q$_{31}$ | 6.2 | 4.2 | 0.2 | 0.6 | 0.9 | 0.5 | 0.7 | 1.8 | 0.7 | 0.1 |  |  | 84.1 |
| Q$_{41}$ | 2.7 | 6.7 | 0.3 | 0.8 | 1.4 | 1.1 | 1.5 | 4.0 | 1.7 | 0.2 | 0.1 | 0.1 | 79.4 |
| Q$_{12}$ | 9.0 | 0.5 |  | 0.1 | 0.2 | 0.2 | 0.3 | 0.7 | 0.3 | 0.1 |  |  | 88.8 |
| Q$_{22}$ | 8.0 | 0.4 |  |  |  | 0.4 | 1.0 | 2.0 | 0.8 | 0.2 |  |  | 87.4 |
| Q$_{32}$ | 5.2 | 1.8 | 0.1 |  | 0.1 | 1.0 | 1.9 | 4.8 | 2.0 | 0.3 |  |  | 82.8 |
| Q$_{42}$ | 5.1 | 1.9 | 0.1 |  | 0.1 | 1.0 | 1.9 | 4.8 | 1.9 | 0.4 |  |  | 82.9 |
| Q$_{13}$ | 6.6 | 2.7 | 0.1 | 0.5 | 0.7 | 0.6 | 0.8 | 2.1 | 0.9 | 0.2 |  |  | 84.7 |
| Q$_{23}$ | 5.6 | 2.3 |  | 0.7 | 1.1 | 0.9 | 1.3 | 3.3 | 1.4 | 0.2 | 0.1 | 0.1 | 83.0 |
| Q$_{33}$ | 5.3 | 2.4 |  | 0.7 | 1.1 | 0.9 | 1.4 | 3.5 | 1.5 | 0.2 | 0.1 | 0.1 | 82.6 |
| Q$_{43}$ | 2.9 | 1.7 |  | 0.6 | 1.9 | 1.8 | 2.5 | 6.5 | 2.9 |  | 0.6 | 0.6 | 78.2 |
| Q$_{14}$ | 6.8 | 1.6 |  | 0.5 | 0.8 | 0.6 | 0.8 | 2.0 | 0.9 | 0.2 | 0.1 | 0.1 | 85.8 |
| Q$_{24}$ | 6.7 | 1.7 |  | 0.5 | 0.8 | 0.6 | 0.8 | 2.2 | 0.9 | 0.2 | 0.1 | 0.1 | 85.4 |
| Q$_{34}$ | 5.8 | 2.2 |  | 0.6 | 0.9 | 0.8 | 1.2 | 3.1 | 1.3 | 0.3 | 0.1 | 0.1 | 83.7 |
| Q$_{44}$ | 5.8 | 3.2 | 0.1 | 0.5 | 1.1 | 0.7 | 1.0 | 2.5 | 1.1 | 0.1 | 0.2 | 0.2 | 83.6 |

TABLE 5

| Hue (Munsell Color System) | Shading Composition |
| --- | --- |
| 8.5 YR | Q$_{11}$, Q$_{21}$, Q$_{31}$, Q$_{41}$ |
| 8.75 YR | Q$_{12}$, Q$_{22}$, Q$_{32}$, Q$_{42}$ |
| 10 YR | Q$_{13}$, Q$_{23}$, Q$_{33}$, Q$_{43}$ |
| 1.25 Y | Q$_{14}$, Q$_{24}$, Q$_{34}$, Q$_{44}$ |

EXAMPLE 5

Preparation of Dental Crown Restoration

The restoration process of the present invention will now be described with reference to the lower central incisor.

1) Selection of Shade Guide

A dentist formed an abutment tooth of the portion to be restored and took the impression. According to the shade guide classification table shown in Table 1, the shade guide matching the color of the adjacent tooth was selected among $Z_{11}$, $Z_{21}$, ... and $Z_{44}$. The dentist wrote the selected shade guide, for example, $Z_{32}$, in prescription. The dentist asked a technician to prepared a restoring dental crown while delivering the prescription and the impression model to a technician.

2) Formation of Working Model

The technician formed a working model from the impression model. The working model was formed to have a color equal or closely akin to the color of a dental cement.

3) Wax-Up

A wax pattern of the incisor was prepared on the working model. The waxed-up incisor was finished to a final form satisfactory in the esthetics and function and from the anatomical viewpoint while taking the relation to the adjacent and occluding teeth into consideration.

4) Embedding

The waxed-up incisor was erected on a sprue former and embedded in a casting embedding material. The mixing ratio of an embedding powder and a hardening agent was 90 g/21 ml. After hardening was conducted for 1 hour, the sprue former was removed, and the embedded incisor was placed in a burning-out furnace (Model CP-RING301 supplied by Denken Co., Ltd.) and maintained at 800° C. for 1 hour to burn out the wax. A casting mold was thus prepared according to the lost-wax method. Then, The casting mold was maintained at 600° C.

5) Selection of Colored Glass Material

The colored glass material $P_3$ corresponding the shade guide $Z_{32}$ instructed by the dentist was selected from the shade guide reproduction-classification table shown in Table 2.

6) Casting

The colored glass material $P_3$ was taken out from the dental crown-restoring kit. The colored glass material $P_3$, which as contained in an alumina crucible, was set in a casting machine (Model CP-CAST701 supplied by Denken Co., Ltd.). The casting mold maintained at 1510° C. for 2 minutes and then maintained at 600° C. was set in the casting machine, and the molten glass was centrifugally cast.

7) Annealing

After the casting, the casting mold was returned into the calcination furnace, and the annealing treatment was immediately carried out. The heat treatment was conducted at 600° C. for 1 hour and at 700° C. for 10 minutes.

8) Crystallization Treatment

The cast product was taken out from the casting mold cooled to room temperature, set in a crystallization furnace (Model CP-CRYSTAL501 supplied by Denken Co., Ltd.) and heat-treated at 900° C. for 1 hour.

9) Shading

The cast dental crown was changed to a yellowish translucent body from the light reddish purple transparent color through the crystallization. The front and inner surfaces were finished by polishing, and the cast product was returned into the working model and the matching state was examined. In order to obtain the shade guide $Z_{32}$ shown in the classification table of FIG. 1, the corresponding shading composition $Q_{32}$ was selected from the reproduction-classification table of FIG. 2. A vessel indicating $Q_{32}$ was taken out from the kit, and the shading composition in this vessel was mixed with a kneading liquid to form a shading paste having a viscosity resembling that of honey. The kneading liquid was a 6/4 liquid mixture of triethanolamine and diacetone alcohol. A white plastic compound was filled in the cast dental crown to support the dental crown, and the shading paste was uniformly coated on the dental crown by a brush. The dental crown was placed on a firing stand of the crystallization furnace and was dried at 500° C. Then, the dental crown was fired at 800° C. for 1 minute and cooled to room temperature. The past-coating and firing operation was repeated 4 times to reproduce the color of the shade guide $Z_{32}$. The dental crown was set on the working model to confirm the color and the like. If there was any problem, shading was further conducted for correction.

10) Installation

The dentist received the finished dental crown from the technician and installed it in the month of a patient by using a white zinc phosphate cement. Before the installation the relation to the occluding and adjacent teeth was adjusted and simultaneously, a mixture of the zinc phosphate cement with glycerol was filled in the interior of the dental crown to check the color. If the color was not matched or polishing was effected for adjustment of the occlusion, the dentist performed shading on the part to be corrected by using the shading powder composition $Q_{32}$ in the same manner as described above in the paragraph (9) (shading step). After the correction, the dental crown was washed and installed in the mouth of the patient by using the zinc phosphate cement.

We claim:

1. A process for the preparation of a dental crown restoration, which comprises preparing a plurality of dental crown-restoring glass materials comprising 100 parts by weight of a glass component and 0.01 to 17.0 parts by weight of an incorporated coloring component and giving colored glass ceramics differing in the value or the combination of the value and chroma in the glass-crystallized state, selecting a shade guide having a color equal or closely akin to the color of a tooth adjacent to the tooth to be restored among a plurality of shade guides classified accord- to a plurality of values or combinations of the value and chroma as one index and a plurality of hues as another index, selecting a glass material giving a predetermined value or a predetermined combination of the value and chroma among said glass materials according to the color of the selected shade guide, preparing a dental crown restoration from the selected glass material, and applying a shading giving a predetermined hue or a predetermined combination of the selected shade guide to the surface of the dental crown restoration.

2. A process according to claim 1, wherein the glass component is a calcium phosphate type glass.

3. A process according to claim 1, wherein the glass component has a composition of $CaO-P_2O_5-MgO-SiO_2$.

4. A process according to claim 1, wherein the dental crown restoration consists of a colored crystallized glass composed mainly of apatite.

5. A process according to claim 1, wherein the transparency (Ts), defined by the following formula, of the colored crystallized glass is 20 to 70%:

$$Ts = (Ys/Yo) \times 100$$

wherein Ys stands for Y value of the tristimulus values of the transmitted light in the standard colorimetric system CIE, measured at a visual field angle 2° by using standard illuminant C with respect to a disk-shaped colored crystallized glass having a thickness of 1.25 mm, and Yo stands for Y value determined with respect to the above-mentioned standard illuminant in the same manner as described above except that the colored crystallized glass is not placed.

6. A process according to claim 1, wherein of the colored crystallized glasses, one having a smallest value has a transparency of 30 to 70% and another having a largest value has a transparency of 20 to 60%.

7. A process according to claim 1, wherein the crystallized glass is composed of a composition comprising 40 to 80% by weight of a $CaO-P_2O_5$ component having a Ca/P atomic ratio of 2.5 to 4.0 and 20 to 60% by weight of an $SiO_2-MgO$ component.

8. A process according to claim 4, wherein the coloring component is at least one member selected from the group consisting of rare earth metal oxides and transition metal oxides.

9. A process according to claim 8, wherein the rare earth metal is selected from the group consisting of Ce, Pr and Eu.

10. A process according to claim 8, wherein the transition metal is selected from the group consisting of Ti, V, Cr, Mn, Fe, Co, Ni, Zr, Nb, Mo, Ag and W.

11. A process according to claim 8, wherein the coloring component is composed of a composition comprising 10 to 70% by weight, based on the coloring component, of $Ce_2O_3$, 30 to 70% by weight, based on the coloring component, of $Mn_3O_4$, up to 40% by weight, based on the coloring component, of $TiO_2$, up to 15% by weight, based on the coloring component, of $Fe_3O_4$ and up to 10% by weight, based on the coloring component, of $V_2O_5$.

12. A process according to claim 1, wherein the preparation of the dental crown restoration is performed by casting a melt of the glass material in a mold having a cavity corresponding to the dental crown and heat-treating the cast product to effect crystallization.

13. A process according to claim 1, wherein the shading is formed by coating a shading composition on the surface of the dental crown restoration and calcining the coated restoration.

14. A process according to claim 13, wherein the shading composition is a composition comprising 60 to 95% by weight of a sodium silicate glass having a melting point of 500° to 1000° C. and 5 to 40% by weight of a coloring agent.

15. A kit for the restoration of dental crowns, which comprises shade guides classified by a plurality of values or a plurality of combinations of the value and chroma as one index and a plurality of hues as another index, a package comprising plurality of crown-restoring glass materials comprising 100 parts by weight of a glass component and 0.01 to 17 parts by weight of an incorporated coloring component and giving colored glass ceramics differing in the value or the combination of the value and chroma in the crystallized state, said glass materials being filled in vessels corresponding to the respective value indexes, and a package comprising a plurality of shading compositions comprising 60 to 95% by weight of a sodium silicate having a melting point of 500° to 1000° C. and 5 to 40% by weight of a coloring agent and differing in the hue or the combination of the hue, value and chroma, said shading compositions being filled in vessels corresponding to the respective hue or value-hue indexes.

16. A kit as set forth in claim 15, wherein the dental crown-restoring glass material is filled in the form of tablets in the vessel and the shading composition is filled in the form of a powder in the vessel.

17. A kit as set forth in claim 15, wherein the vessel for filling the dental crown-restoring glass material also acts as a crucible for melting the glass material.

18. An artificial tooth consisting of a colored crystallized glass composed mainly of apatite, said colored glass comprising 100 parts by weight of a glass component and 0.01 to 17 parts by weight of a coloring component, said glass component comprising 40 to 80% by weight of a $CaO-P_2O_5$ component having a Ca/P atomic ratio of 2.5 to 4.0 and 20 to 60% by weight of an SiO$_2$-MgO component, and said coloring component being an oxide of at least one metal selected from the group consisting of Ce, Pr, Eu, Ti, V, Cr, Mn, Fe, Co, Ni, Zr, Nb, Mo, Ag and W.

19. An artificial tooth as set forth in claim 18, wherein the transparency (Ts), defined by the following formula, of the colored crystallized glass is 20 to 70%:

$$Ts = (Ys/Yo) \times 100$$

wherein Ys stands for Y value of the tristimulus values of the transmitted light in the standard colorimetric system CIE, measured at a visual field angle 2° by using standard illuminant C with respect to a disk-shaped colored crystallized glass having a thickness of 1.25 mm, and Yo stands for Y value determined with respect to the above-mentioned standard illuminant in the same manner as described above except that the colored crystallized glass is not placed.

20. An artificial tooth as set forth in claim 18, wherein a shading layer is formed on the outer surface of the artificial tooth substrate.

* * * * *